US00PP25579P2

(12) United States Plant Patent
Eveleens

(10) Patent No.: US PP25,579 P2
(45) Date of Patent: May 26, 2015

(54) ***HYDRANGEA* PLANT NAMED 'HORTMABRID'**

(50) Latin Name: *Hydrangea macrophylla*
Varietal Denomination: HORTMABRID

(71) Applicants: Horteve Breeding BV, De Kwakel (NL); Kolster Holding BV, Boskoop (NL)

(72) Inventor: Cornelis Pieter Eveleens, De Kwakel (NL)

(73) Assignees: Horteve Breeding BV, De Kwakel (NL), part interest; Kolster Holding BV, Boskoop (NL), part interest ( * ) Notice: Subject to any disclaimer, the term of this patent is extended or adjusted under 35 U.S.C. 154(b) by 89 days.

(21) Appl. No.: 13/998,082

(22) Filed: Sep. 30, 2013

(51) Int. Cl.
*A01H 5/00* (2006.01)

(52) U.S. Cl.
USPC ..... Plt./250

(58) Field of Classification Search
CPC ..... A01H 5/02; A01H 5/00
USPC ..... Plt./250
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* named 'HORTMABRID' that is characterized by its globular shaped inflorescence, its very sturdy sterile flowers, its sterile flowers with bright pure white sepals that have a high tolerance to sunlight, and its good cut flower quality lasting at least 2 weeks as a fresh cut (white color) and for many months when flowers age (when classic green).

2 Drawing Sheets

Botanical classification: *Hydrangea macrophylla.*
Varietal denomination: 'HORTMABRID'.

BACKGROUND OF THE INVENTION

The present invention relates to a new and distinct cultivar of *Hydrangea macrophylla* and will be referred to hereafter by its cultivar name, 'HORTMABRID'. 'HORTMABRID' represents a new mophead type *Hydrangea*, a deciduous shrub grown for use as a landscape plant, potted plant and as a cut flower.

The new cultivar was derived from a controlled breeding program conducted by the Inventor in Boskoop, The Netherlands. The Inventor made a cross in May 2004 between unnamed proprietary plants in the Inventor's breeding program, reference no. 02-011-01, as the female parent and reference no. 97-028-13 as the male parent. The Inventor selected 'HORTMABRID', in June 2012 as a single unique plant amongst the seedlings that resulted from the above cross.

Asexual propagation of the new cultivar was first accomplished by the Inventor by softwood stem cuttings in Boskoop, The Netherlands in July 2006. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HORTMABRID' as a unique cultivar of *Hydrangea.*

1. 'HORTMABRID' exhibits a globular shaped inflorescence.

2. 'HORTMABRID' exhibits very sturdy sterile flowers both as fresh flowers and as they become classic (aged form).
3. 'HORTMABRID' exhibits sterile flowers with bright and pure white sepals that have a high tolerance to sunlight.
4. 'HORTMABRID' exhibits a good cut flower quality lasting at least 2 weeks as a fresh cut (white color) and for many months when flowers age (when classic green).

The female parent of 'HORTMABRID', reference no. 02-011-01, differs from 'HORTMABRID' in having sterile flowers with softer sepals that are more susceptible to burning in sunlight. The male parent of 'HORTMABRID', reference no. 97-028-13, differs from 'HORTMABRID' in having pink sterile flowers and in flowering later in the season. 'HORTMABRID' can be most closely compared to the cultivars 'Napo' (U.S. Plant Pat. No. 20,614) and 'Snowball' (not patented). 'Napo' is similar to 'HORTMABRID' in having white flowers and in having sturdy sterile flowers. 'Napo' differs from 'HORTMABRID' in being shorter in height, in having sterile flowers with smaller sepals, and in having more flowers per inflorescence. 'Snowball' is similar to 'HORTMABRID' in having white flowers. 'Snowball' differs from 'HORTMABRID' in being much taller in height and in having sterile flowers that fade and are of less quality as the flowers mature.

BRIEF DESCRIPTION OF THE DRAWINGS

The accompanying colored photographs illustrate the overall appearance and distinct characteristics of the new *Hydrangea*, 'HORTMABRID', as grown in a 17-cm container in a shaded greenhouse in Boskoop, The Netherlands. The photographs were taken of a two year-old plant of 'HORTMABRID' as grown in a 17-cm container.

The photograph in FIG. 1 provides a side view of a plant of 'HORTMABRID'.

Figure 1:
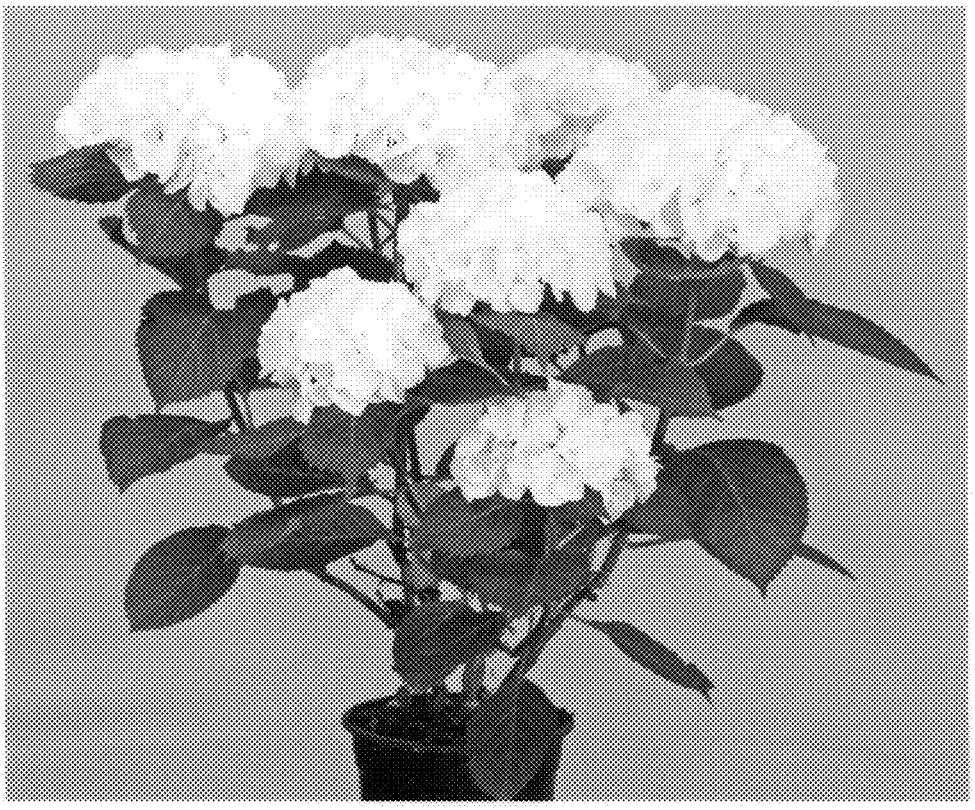
Figure 2:
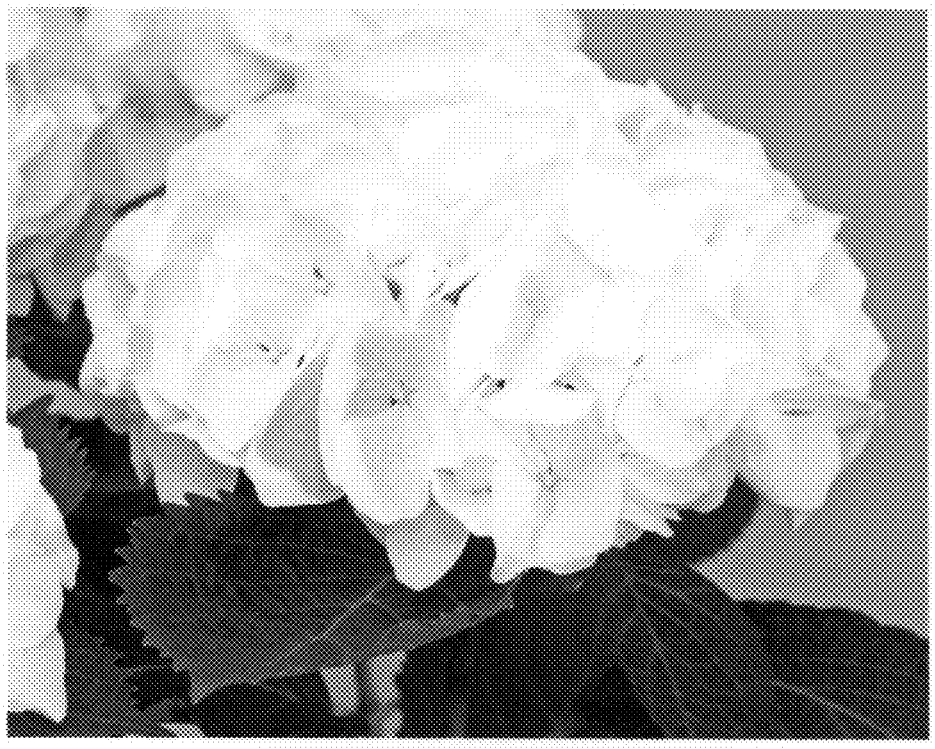

The photograph in FIG. 2 provides a close-up view of an inflorescence of 'HORTMABRID'.

Figure 3:
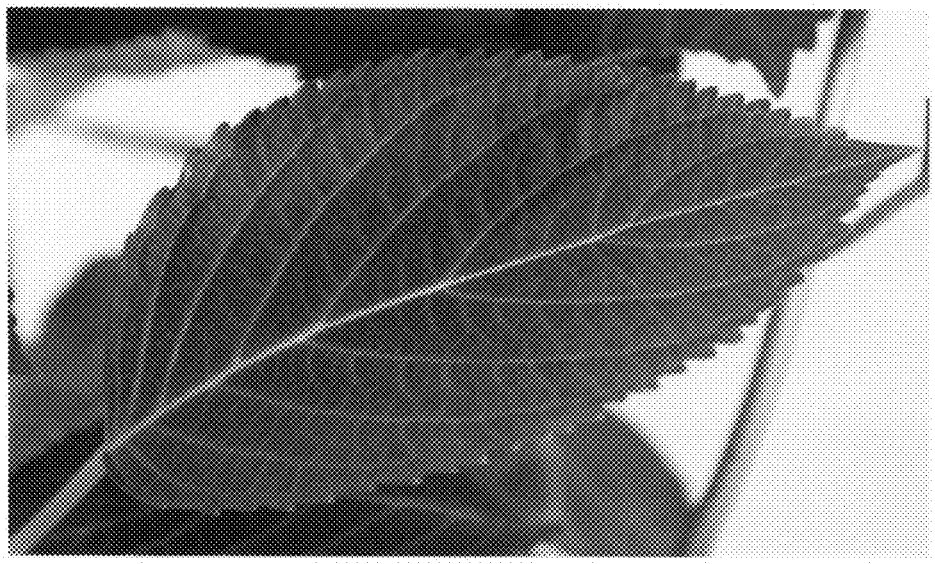

The photograph in FIG. 3 provides a close-up view of the foliage of 'HORTMABRID'.

The colors in the photographs may differ slightly from the color values cited in the detailed botanical description, which accurately describe the colors of the new *Hydrangea*.

BOTANICAL DESCRIPTION OF THE PLANT

The following is a detailed description of two year-old plants of 'HORTMABRID' as grown in a shaded greenhouse in 17-cm containers in Boskoop, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period*.—Commences in May and blooms for 4 months as greenhouse grown plants in Boskoop, the Netherlands.

*Plant type*.—Deciduous shrub, mophead type *Hydrangea*.

*Plant habit*.—Broad upright.

*Height and spread*.—Reaches about 46 cm in height and 64 cm in spread.

*Hardiness*.—At least in U.S.D.A. Zones 5 to 9.

*Environmental conditions*.—Flowers have a high tolerance to sunlight, moderate tolerance to wind, and moderate to high tolerance to rain.

*Diseases resistance*.—No particular susceptibility or resistance to diseases or pests has been observed.

*Root description*.—Fine and fibrous.

*Propagation*.—Softwood stem cuttings.

*Growth rate and vigor*.—Moderate.

Stem description:

*Stem shape*.—Rounded.

*Stem strength*.—Strong.

*Stem color*.—New growth; 144A to 144B suffused with 187B to 187C at the nodes, mature growth; a blend of 165B to 165C and N199D.

*Stem size*.—Average of 32.2 cm in length and 7 mm in diameter.

*Stem surface*.—Glabrous, sparsely to moderately lenticellate, lenticles; 5 per $cm^2$, an average of 2 mm in length and 1 mm in width, N186C in color.

*Internode length*.—Average of 6 cm.

*Branching*.—Average of 7 lateral branches without pinching.

Foliage description:

*Leaf shape*.—Ovate to broad ovate.

*Leaf arrangement*.—Opposite.

*Leaf division*.—Simple.

*Leaf base*.—Obtuse to short attenuate.

*Leaf apex*.—Broad apiculate.

*Leaf margins*.—Serrate.

*Leaf venation*.—Pinnate, upper surface 144C and lower surface a blend of 144D and 145B in color.

*Leaf size*.—Matures to an average of 13.3 cm in length and 9 cm in width.

*Leaf attachment*.—Petiolate.

*Leaf surface*.—Upper and lower surface; glabrous and very slightly rugose.

*Leaf color*.—Young foliage upper surface a blend of 143C and 144A and young foliage lower surface; 144A to 144B, mature foliage upper surface; N137A, mature foliage lower surface; 147B.

*Petioles*.—An average of 3.2 cm in length and 3 mm in diameter, color; upper surface 144B and lower surface 145A, surface glabrous and moderately glossy.

Inflorescence description:

*Inflorescence type*.—Terminal panicle, mophead in form comprised of a center region of fertile flowers surrounded by many single sterile flowers.

*Lastingness of inflorescence*.—Persistent for 4 months with white coloration retained for about 6 weeks (depending on growing conditions).

*Lastingness as a cut flower*.—White color is retained for 2 weeks as a fresh cut and for several months as an aged flower (when "classic").

*Inflorescence substance*.—Sturdy sterile flowers as the sepals do not turn upside down or brown with age (classic).

*Inflorescence number*.—One per lateral or sublateral stem if pinched.

*Inflorescence size*.—Average of 11.4 cm in height and 19.7 cm in diameter.

*Flower number*.—Average of 180 sterile flowers and 60 fertile flowers per panicle.

*Flower fragrance*.—None.

*Flower aspect*.—Upright to outward and slightly drooping.

*Flower size*.—Sterile flowers; an average of 4.7 cm in diameter and 1.5 mm in depth, fertile flowers; an average of 9 mm in diameter and 9 mm in depth.

*Flower type*.—Rotate.

*Flower buds*.—Sterile flowers; average of 9 mm in length and diameter prior to opening, ovate in shape, 145D in color, fertile flowers; average of 3.5 mm in length and 4 mm in diameter, broad obovate in shape, 145D in color.

*Peduncles*.—Moderately strong, average of 3 cm in length and 2 mm in width, blend of 157C to 157D and 155A in color, surface is dull and glabrous.

*Pedicels*.—Sterile flowers; held at an average angle of 30° from vertical, an average of 2 cm in length and 1.5 mm in diameter, strong strength, NN155C to NN155D in color, surface glabrous, dull, and covered with lenticels an average of 0.5 mm in length and width, 61D in color, fertile flowers; held at an average angle of 15° from vertical, an average of 3 mm in length and 1 mm in diameter, moderate strength, a blend of 157C to 157D and 155A in color, surface is dull and glabrous.

*Petals*.—Fertile flowers; average of 5, rotate in arrangement, ovate and concave in shape, entire margin, acute apex, cuneate base, average of 4 mm in length and 2 mm in width, upper and lower surface glabrous and dull, color of upper and lower surface when opening and when fully opened NN155C to NN155D, color not fading, sterile flowers; an average of 5, rotate arrangement, acute apex, cuneate base, entire margins, ovate and concave in shape, an average of 3 mm in length and 2 mm in width, upper and lower surface; glabrous and dull, color; upper and lower surface when opening and when fully open NN155C to NN155D, color not fading.

*Sepals*.—Sterile flowers; average of 4, rotate arrangement, broad rhomboidal to deltoid in shape, an average of 3 cm in length and 3.4 cm in width, broad bluntly acute apex, short acuminate base, upper and lower surface glabrous and dull, entire margins, color when opening upper surface; NN155D and lower surface; NN155C to NN155D, color when fully opened upper surface; NN155B to NN155C and lower surface; NN155B with NN155A to NN155B towards the margins, color changes to 145B on upper and lower surface, fertile flowers; 5, rotate in arrangement, ovate in shape, entire margin, acute apex, broad cuneate base, average of 3 mm in length and 0.15 mm in width, both surfaces are glabrous and dull, color of upper and lower surface when opening 157C to 157D, color of upper and lower surface when fully opened 157A to 157B.

Reproductive organs: (present on fertile flowers and occasionally on sterile flowers).

*Stamens*.—Sterile flowers; average of 8, anther is broad reniform in shape, an average of 0.5 mm in length and NN155A in color, filament is 3 mm in length and NN155D in color, pollen is low to moderate in quantity and 155A in color, fertile flowers; average of 10, anther is broad reniform in shape, 05 mm in length and NN155A in color, filament is 3.5 mm in length and NN155D in color, pollen is moderate in quantity and 155A in color.

*Pistils*.—Sterile flowers; average of 3, an average of 1 mm in length, stigma is clavate in shape and NN155C to NN155D in color, style is an average of 0.5 mm in length and 157D in color, ovary is 157D in color, fertile flowers; average of 3, an average of 1.5 mm in length, stigma is clavate in shape and NN155C to NN155D in color, style is an average of 1 mm in length and 157D in color, ovary is 157C in color.

*Fruit and seed*.—Has not been observed to date.

It is claimed:

1. A new and distinct cultivar of *Hydrangea* plant named 'HORTMABRID' substantially as herein illustrated and described.

* * * * *